(12) United States Patent
Ramos-Stanbury et al.

(10) Patent No.: US 10,076,472 B2
(45) Date of Patent: Sep. 18, 2018

(54) AQUEOUS COMPOSITION COMPRISING HYDROPHOBIC SILICA AEROGEL PARTICLES, A DEODORANT AGENT AND/OR AN ANTIPERSPIRANT ACTIVE AGENT AND A SPECIFIC ALCOHOL

(71) Applicant: L'OREAL, Paris (FR)

(72) Inventors: Laure Ramos-Stanbury, Sceaux (FR); Odile Aubrun, Antony (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/783,566

(22) PCT Filed: Mar. 20, 2014

(86) PCT No.: PCT/EP2014/055583
§ 371 (c)(1),
(2) Date: Oct. 9, 2015

(87) PCT Pub. No.: WO2014/166716
PCT Pub. Date: Oct. 16, 2014

(65) Prior Publication Data
US 2016/0081889 A1 Mar. 24, 2016

(30) Foreign Application Priority Data

Apr. 11, 2013 (FR) ...................... 13 53297

(51) Int. Cl.
| | | |
|---|---|---|
| *A61K 8/04* | (2006.01) | |
| *A61K 8/26* | (2006.01) | |
| A61K 8/58 | (2006.01) | |
| *A61K 8/365* | (2006.01) | |
| *A61K 8/25* | (2006.01) | |
| *A61K 8/02* | (2006.01) | |
| *A61K 8/49* | (2006.01) | |
| *A61K 8/39* | (2006.01) | |
| *A61K 8/34* | (2006.01) | |
| *A61Q 15/00* | (2006.01) | |

(52) U.S. Cl.
CPC ............ *A61K 8/042* (2013.01); *A61K 8/0279* (2013.01); *A61K 8/25* (2013.01); *A61K 8/26* (2013.01); *A61K 8/34* (2013.01); *A61K 8/345* (2013.01); *A61K 8/365* (2013.01); *A61K 8/39* (2013.01); *A61K 8/4913* (2013.01); *A61K 8/58* (2013.01); *A61K 8/585* (2013.01); *A61Q 15/00* (2013.01); *A61K 2800/412* (2013.01); *A61K 2800/612* (2013.01)

(58) Field of Classification Search
CPC ........ A61K 2800/412; A61K 2800/612; A61K 8/0279; A61K 8/042; A61K 8/25; A61K 8/26; A61K 8/34; A61K 8/345; A61K 8/365; A61K 8/39; A61K 8/4913; A61K 8/58; A61K 8/585; A61Q 15/00
See application file for complete search history.

(56) References Cited

U.S. PATENT DOCUMENTS

| 6,001,341 A * | 12/1999 | Genova | ..................... A61K 8/37 424/401 |
|---|---|---|---|
| 6,261,543 B1 * | 7/2001 | Fletcher | ................... A61K 8/26 424/400 |
| 2002/0048597 A1 * | 4/2002 | Kropke | ..................... A61K 8/06 424/450 |

FOREIGN PATENT DOCUMENTS

| WO | WO 2012/084781 A2 * | 6/2012 | ............... A61K 8/25 |
|---|---|---|---|
| WO | WO 2013/076674 A1 * | 5/2013 | ............... A61K 8/06 |

* cited by examiner

*Primary Examiner* — Aradhana Sasan
(74) *Attorney, Agent, or Firm* — Polsinelli PC

(57) ABSTRACT

A subject of the present invention is therefore a composition comprising, in a cosmetically acceptable medium: a) an aqueous phase and b) at least hydrophobic silica aerogel particles and; c) at least one alcohol of formula (I) below and also optical isomers thereof:

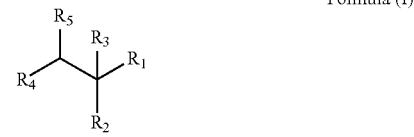

Formula (I)

$R_1$ represents an —OH or $CH_2OH$ group;
$R_2$ represents a hydrogen atom or an —OH group;
$R_3$ represents a hydrogen atom or a linear or branched, saturated or unsaturated $C_1$-$C_{22}$ alkyl group;
$R_4$ represents a hydrogen atom, an —OH group, a —$CH_2OH$ group, a —CH(OH)—$CH_3$ group, a —$C(CH_3)_2$—OH group, a —(O)—$CH_2$—$CH_2)_n$—OH group, a —(O—$CH_2$—$CH(CH_3))_m$—OH group or a —($CH_2$—$CH_2)_p$—OH group;
n denotes an integer ranging from 1 to 10;
m denotes an integer ranging from 1 to 10;
p denotes an integer ranging from 1 to 5;
with the proviso that at least one of the radicals $R_1$, $R_2$, $R_3$ and $R_4$ comprises at least one hydroxyl function;
$R_5$ represents a hydrogen atom or a linear or branched, saturated or unsaturated $C_1$-$C_{22}$ alkyl group and
d) at least one deodorant active agent other than said alcohol of formula (I) and/or at least one antiperspirant active agent; said hydrophobic silica aerogel particles being dispersed in the aqueous phase. The present invention relates to a cosmetic treatment process for a keratin material for treating body odors associated with human perspiration, in particular underarm odors and optionally for treating human perspiration, which consists in applying, to the surface of said keratin material to be treated, at least one composition as defined above.

24 Claims, No Drawings

AQUEOUS COMPOSITION COMPRISING HYDROPHOBIC SILICA AEROGEL PARTICLES, A DEODORANT AGENT AND/OR AN ANTIPERSPIRANT ACTIVE AGENT AND A SPECIFIC ALCOHOL

CROSS REFERENCE TO RELATED APPLICATIONS

This application is a National Phase filing under 35 U.S.C. § 371 of PCT/EP2014/055583 filed on Mar. 20, 2014; and this application claims priority to Application No. 1353297 filed in France on Apr. 11, 2013. The entire contents of each application are hereby incorporated by reference.

The invention relates to a composition comprising, in a cosmetically acceptable medium:
 a) an aqueous phase and
 b) at least hydrophobic silica aerogel particles and
 c) at least one alcohol of formula (I) that will be defined in detail later and
 d) at least one deodorant active agent other than said alcohol of formula (I) and/or at least one antiperspirant active agent; said hydrophobic silica aerogel particles being dispersed in the aqueous phase.

The present invention relates to a cosmetic treatment process for a keratin material for treating body odours associated with human perspiration, in particular underarm odours and optionally human perspiration, which consists in applying, to the surface of the keratin material to be treated, at least one composition as defined above.

Eccrine or apocrine sweat has little odour when it is secreted. It is its degradation by bacteria via enzymatic reactions that produces malodorous compounds.

Deodorants have the function of reducing or preventing the formation of unpleasant odours. This objective can be achieved in particular through a deodorant and/or antiperspirant activity.

Antiperspirant substances have the effect of limiting the flow of sweat. They generally consist of aluminium salts which, on the one hand, are potentially irritant to the skin and which, on the other hand, reduce the flow of sweat by modifying the physiology of the skin, which is unsatisfactory.

Deodorant activity can be obtained by various mechanisms, in particular:
 by odour absorption,
 by neutralisation of the volatile compounds responsible for the odour,
 by inhibition of the enzymes responsible for the formation of the odorous compounds, and/or
 by bactericidal action, which is preferably selective for the strains responsible for the odours, or which reduces bacterial growth.

Deodorant products are generally available in the form of roll-ons, tubes, sticks, aerosols or sprays. The galenical formulations most effective for combating unpleasant odour are alcoholic galenical formulations. They have the drawback of causing discomfort at the moment of application, in particular after shaving of the armpit. Emulsions have the drawback of being wetting and of drying with difficulty under the armpit. Anhydrous sticks and aerosols are fatty galenical formulations which leave a greasy feel under the armpit.

Patent application WO 2012/084520 describes solid soft (semi/soft) anhydrous compositions based on hydrophobic silica aerogel particles, that after application give a dry and greasy feel. Patent application WO 2012/084522 has also proposed the use of hydrophobic silica aerogel particles as deodorant active agent in anhydrous roll-ons or anhydrous aerosol formulae; these compositions have the drawback of giving a greasy feel.

There is a real need to have access to galenical formulations which have good deodorant efficiency providing freshness, while at the same time being sparingly wetting and having an immediate dry effect.

The applicant has discovered, surprisingly, that this objective can be achieved with a composition comprising, in a cosmetically acceptable medium:
 a) an aqueous phase,
 b) at least hydrophobic silica aerogel particles and
 c) at least one alcohol of formula (I) that will be defined in detail later and
 d) at least one deodorant active agent other than said alcohol of formula (I) and/or at least one antiperspirant active agent; said hydrophobic silica aerogel particles being dispersed in the aqueous phase.

This discovery is the basis of the invention.

A subject of the present invention is therefore a composition comprising, in a cosmetically acceptable medium:
 a) an aqueous phase and
 b) at least hydrophobic silica aerogel particles and
 c) at least one alcohol of formula (I) that will be defined in detail later and
 d) at least one deodorant active agent other than said alcohol of formula (I) and/or at least one antiperspirant active agent.

The present invention relates to a cosmetic treatment process for a keratin material for treating body odours associated with human perspiration, in particular underarm odours and optionally for treating human perspiration, which consists in applying, to the surface of the keratin material to be treated, at least one composition as defined above.

For the purposes of the present invention, the term "cosmetically acceptable medium" is intended to mean a medium that is suitable for the topical administration of a composition. A physiologically acceptable medium is preferentially a cosmetically or dermatologically acceptable medium, that is to say a medium which is devoid of unpleasant odour or appearance and which is entirely compatible with the topical administration route. In the present case, where the composition is intended for topical administration, that is to say for administration by application at the surface of the keratin material under consideration, such a medium is considered in particular to be physiologically acceptable when it does not cause stinging, tightness or redness unacceptable to the user.

For the purposes of the present invention, the expression "hydrophobic silica aerogel particles dispersed in the aqueous phase" is intended to denote hydrophobic silica aerogel particles of which the entire population is uniformly distributed in the aqueous phase. Thus, compositions in oil/water emulsion form are not part of the present invention.

The term "aqueous phase" is intended to mean the mixture consisting of water and the water-soluble cosmetic or dermatological ingredients.

The term "keratin material" is intended to mean the skin (of the body, face and around the eyes), hair, eyelashes, eyebrows, bodily hair, nails, lips or mucous membranes.

The term "deodorant active agent" is intended to mean any substance capable of reducing, masking or absorbing human body odours, in particular underarm odours.

The term "antiperspirant active agent" is intended to mean any aluminium salt or complex which, by itself alone, has the effect of reducing the flow of sweat, of reducing the sensation on the skin of moisture associated with human sweat and of masking human sweat.

Hydrophobic Silica Aerogel Particles

The composition according to the invention comprises hydrophobic silica aerogel particles. These are preferably in a dispersion in the aqueous phase of the composition.

Aerogels are ultra-light porous materials, the first ones of which were made by Kristler in 1932.

They are generally synthesized via a sol-gel process in liquid medium and then dried by extraction of a supercritical fluid. The supercritical fluid most commonly used is supercritical $CO_2$. This type of drying makes it possible to avoid shrinkage of the pores and of the material.

Other types of drying also make it possible to obtain porous materials from gel, namely (i) drying by cryodesiccation, which consists in solidifying the gel at low temperature and then in sublimating off the solvent, and (ii) drying by evaporation. The materials thus obtained are then known, respectively, as cryogels and xerogels. The sol-gel process and the various drying processes are described in detail in Brinker C J., and Scherer G. W., Sol-Gel Science: New York: Academic Press, 1990.

The term "hydrophobic silica" is intended to mean any silica of which the surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

Preferably, the hydrophobic aerogel particles which can be used in the present invention advantageously have a specific surface area per unit of mass (SM) ranging from 500 to 1500 $m^2/g$, preferably from 600 to 1200 $m^2/g$ and better still from 600 to 800 $m^2/g$ and/or have an oil absorption capacity measured at the wet point ranging from 5 to 18 ml/g of particles, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or the method for determining the oil uptake of a powder according to the principle described in standard NF T 30-022. It corresponds to the amount of oil adsorbed onto the available surface of the powder and/or absorbed by the powder by measurement of the wet point, described below:

An amount m=2 g of powder is placed on a glass plate, and the oil (isononyl isononanoate) is then added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The hydrophobic silica aerogel particles used according to the present invention are preferably silylated silica aerogel particles (INCI name: silica silylate).

The preparation of hydrophobic silica aerogel particles that have been surface-modified by silylation is described more fully in U.S. Pat. No. 7,470,725.

Use will be made in particular of aerogel particles of hydrophobic silica surface-modified with trimethylsilyl groups.

The hydrophobic aerogel particles that may be used in the present invention advantageously have a size, expressed as the mean diameter (D[0.5]), of less than 1500 μm, and preferably ranging from 1 to 30 μm, preferably from 5 to 25 μm, better still from 5 to 20 μm and even better still from 5 to 15 μm.

The specific surface area per unit of mass can be determined by the nitrogen absorption method, known as the BET (Brunauer-Emmett-Teller) method, described in The Journal of the American Chemical Society, vol. 60, page 309, February 1938, which corresponds to International Standard ISO 5794/1 (appendix D). The BET specific surface area corresponds to the total specific surface area of the particles under consideration.

The sizes of the aerogel particles according to the invention may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

According to one advantageous embodiment, the hydrophobic aerogel particles used in the present invention have a specific surface area per unit of mass (SM) ranging from 600 to 800 $m^2/g$ and a size, expressed as the volume mean diameter (D[0.5]), ranging from 5 to 20 μm and better still from 5 to 15 μm.

According to one preferred embodiment, use will be made more particularly of VM-2270, the particles of which have a mean size ranging from 5 to 15 microns and a specific surface area per unit of mass ranging from 600 to 800 $m^2/g$.

The hydrophobic aerogel particles used in the present invention may advantageously have a tamped density ρ ranging from 0.04 $g/cm^3$ to 0.10 $g/cm^3$ and preferably from 0.05 $g/cm^3$ to 0.08 $g/cm^3$.

In the context of the present invention, this density may be assessed according to the following protocol, known as the tamped density protocol:

40 g of powder are poured into a measuring cylinder and the cylinder is then placed on a Stav 2003 machine from Stampf Volumeter. The cylinder is then subjected to a series of 2500 tamping actions (this operation is repeated until the difference in volume between two consecutive tests is less than 2%); the final volume Vf of tamped powder is then measured directly on the cylinder.

The tamped density is determined by the ratio: mass (m)/Vf, in this instance 40/Vf (Vf being expressed in $cm^3$ and m in g).

According to one embodiment, the hydrophobic aerogel particles used in the present invention have a specific surface area per unit of volume SV ranging from 5 to 60 $m^2/cm^3$, preferably from 10 to 50 $m^2/cm^3$ and better still from 15 to 40 $m^2/cm^3$.

The specific surface area per unit of volume is given by the relationship:

$$SV = SM \times \rho$$

where ρ is the tamped density expressed in $g/cm^3$ and SM is the specific surface area per unit of mass expressed in $m^2/g$, as defined above.

According to one preferred embodiment, the hydrophobic aerogel particles according to the invention have a specific surface area per unit of mass (SM) ranging from 500 to 1500 m$^2$/g, preferably from 600 to 1200 m$^2$/g and better still from 600 to 800 m$^2$/g, and have a size, expressed as the mean diameter (D[0.5]), ranging from 1 to 30 μm and/or an oil absorption capacity, measured at the wet point, ranging from 5 to 18 ml/g of particles, preferably from 6 to 15 ml/g and better still from 8 to 12 ml/g.

As hydrophobic silica aerogels that may be used in the invention, examples that may be mentioned include the aerogel sold under the name VM-2260 (INCI name: Silica silylate), by the company Dow Corning, the particles of which have an average size of about 1000 microns and a specific surface area per unit of mass ranging from 600 to 800 m$^2$/g.

Mention may also be made of the aerogels sold by the company Cabot under the references Aerogel TLD 201, Aerogel OGD 201 and Aerogel TLD 203, Enova Aerogel MT 1100 and Enova Aerogel MT 1200.

Use will be made more particularly of the aerogel sold under the name VM-2270 (INCI name: Silica silylate), by the company Dow Corning, the particles of which have an average size ranging from 5 to 15 microns and a specific surface area per unit of mass ranging from 600 to 800 m$^2$/g.

The hydrophobic silica aerogel particles are used in a content preferably ranging from 0.05% to 10% by weight, more preferentially from 0.1% to 5% and even more preferentially from 0.5% to 4% by weight relative to the total weight of the composition.

Alcohols

The alcohols in accordance with the present invention correspond to general formula (I) and also optical isomers thereof:

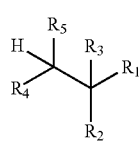

Formula (I)

$R_1$ represents a hydrogen atom or a CH$_2$OH group;
$R_2$ represents a hydrogen atom or an —OH group;
$R_3$ represents a hydrogen atom or a linear or branched, saturated or unsaturated C$_1$-C$_5$ alkyl group;
$R_4$ represents a hydrogen atom, an —OH group, a —CH$_2$OH group, a —CH(OH)—CH$_3$ group, a —C(CH$_3$)$_2$—OH group, a —(O—CH$_2$—CH$_2$)$_n$—OH group, a —(O—CH$_2$—CH(CH$_3$))$_m$—OH group or a —(CH$_2$—CH$_2$)$_p$—OH group; n denotes an integer ranging from 1 to 10;
m denotes an integer ranging from 1 to 10;
p denotes an integer ranging from 1 to 5;
with the proviso that at least one of the radicals $R_1$, $R_2$, $R_3$ and $R_4$ comprises at least one hydroxyl function;
$R_5$ represents a hydrogen atom or a linear or branched, saturated or unsaturated C$_1$-C$_5$ alkyl group.

Use will more preferentially be made of ethanol, propylene glycol, 1,3 butylene glycol, pentylene glycol, hexylene glycol, dipropylene glycol, propane-1,3-diol, PEG-8, glycerol or mixtures thereof.

Use will even more preferentially be made of ethanol, propylene glycol, hexylene glycol, glycerol or mixtures thereof.

The alcohol(s) of formula (I) is (are) preferably present in a content of from 0.1% to 80% by weight and more preferentially from 0.5% to 60% by weight relative to the total weight of the composition.

Aqueous Phase

The aqueous phase preferably represents at least 90% by weight and preferably between 90% and 98% relative to the total weight of the composition.

Deodorant Active Agents

According to one particular form of the invention, the compositions may contain at least one deodorant active agent other than the alcohol of formula (I).

The term "deodorant active agent" is intended to mean any substance capable of reducing, masking or absorbing human body odours, in particular underarm odours.

The deodorant active agents may be bacteriostatic agents or bactericidal agents which act on the microorganisms of armpit odours, for instance 2,4,4'-trichloro-2'-hydroxydiphenyl ether (Triclosan®), 2,4-dichloro-2'-hydroxydiphenyl ether, 3',4',5'-trichlorosalicylanilide, 1-(3',4'-dichlorophenyl)-3-(4'-chlorophenyl)urea (Triclocarban®) or 3,7,11-trimethyldodeca-2,5,10-trienol (Farnesol®); quaternary ammonium salts, for instance cetyltrimethylammonium salts, cetylpyridinium salts, 1,2 decanediol (SYMCLARIOL from the company Symrise), ethyllauroyl arginate hydrochloride (Aminat G sold by Vedeqsa); lichen extract, for instance the product sold under the reference Usneo by Cosmetochem; glyceryl derivatives, for instance caprylic/capric glycerides (Capmul MCM® from Abitec), glyeryl caprate or caprylate (Dermosoft GMCY® and Dermosoft GMC® from Straetmans), polyglyceryl-2 caprate (Dermosoft DGMC® from Straetmans), biguanide derivatives, for instance polyhexamethylene biguanide salts; chlorhexidine and salts thereof; 4-phenyl-4,4-dimethyl-2-butanol (Symdeo MPP® from Symrise); zinc salts, for instance zinc salicylate, zinc gluconate, zinc pidolate, zinc sulfate, zinc chloride, zinc lactate, zinc phenolsulfonate; salicylic acid and derivatives thereof such as 5-n-octanoylsalicylic acid (or 5-n-capryloylsalicylic acid) having the INCI name Capryloyl Salicylic Acid and manufactured under the trade name Mexoryl SAB® by Chimex.

The deodorant active agents may be odour neutralizers or absorbers, for instance zinc ricinoleates, sodium bicarbonate; silver or metallic or non-silver zeolites, cyclodextrins and derivatives thereof. They may also be chelating agents, such as the tetrasodium glutamate diacetate sold under the trade name Dissolvine GL-47-S® by Akzo Nobel, ethylenediaminetetraacetic acid and also salts (EDTA), or ethylenediaminepentaacetic acid and also salts (DPTA).

It may also be an enzyme inhibitor such as triethyl citrate.

Zinc pidolate, calcium chloride, zinc gluconate, triethyl citrate, 5-n-capryloylsalicylic acid or mixtures thereof will more particularly be used as deodorant active agents.

In the event of incompatibility and/or to stabilize them, for example, some of the active agents mentioned above may be incorporated into spherules, in particular ionic or non-ionic vesicles.

The deodorant active agents may be present in the composition according to the invention in a proportion of from 0.001% to 40% by weight relative to the total weight of the composition, and preferably in a proportion of from 0.1% to 25% by weight.

Antiperspirant Active Agents

The compositions contain at least one antiperspirant aluminium and/or zirconium salt.

They are preferably chosen from aluminium and/or zirconium salts; complexes of zirconium hydroxychloride and of aluminium hydroxychloride with an amino acid, such as those described in U.S. Pat. No. 3,792,068, commonly known as "ZAG complexes". Such complexes are generally known under the name "ZAG" (when the amino acid is glycine). ZAG complexes ordinarily have an Al/Zr quotient ranging from about 1.67 to 12.5 and a metal/Cl quotient ranging from about 0.73 to 1.93. Among these products, mention may be made of aluminium zirconium octachlorohydrex GLY, aluminium zirconium pentachlorohydrex GLY, aluminium zirconium tetrachlorohydrate GLY and aluminium zirconium trichlorohydrate GLY.

Among the aluminium salts that may be mentioned are aluminium chlorohydrate, aluminium chlorohydrex, aluminium chlorohydrex PEG, aluminium chlorohydrex PG, aluminium dichlorohydrate, aluminium dichlorohydrex PEG, aluminium dichlorohydrex PG, aluminium sesquichlorohydrate, aluminium sesquichlorohydrex PEG, aluminium sesquichlorohydrex PG, alum salts, aluminium sulfate, aluminium zirconium octachlorohydrate, aluminium zirconium pentachlorohydrate, aluminium zirconium tetrachlorohydrate, aluminium zirconium trichlorohydrate and more particularly the aluminium chlorohydrate in activated or non-activated form sold by the company Reheis under the name Microdry Aluminum Chlorohydrate® or by the company Guilini Chemie under the name Aloxicoll PF 40. Aluminium and zirconium salts are, for example, the product sold by the company Reheis under the name Reach AZP-908-SUF®, "activated" aluminium salts, for example the product sold by the company Reheis under the name Reach 103 or by the company Westwood under the name Westchlor 200.

Aluminium chlorohydrate will more particularly be used.

The antiperspirant active agents, salts or complexes may be present in the composition according to the invention in a proportion of from 0.5% to 25% by weight relative to the total weight of the composition.

Additives

The cosmetic compositions according to the invention may also comprise cosmetic adjuvants chosen from emollients, antioxidants, opacifiers, stabilizers, moisturizers, vitamins, preserving agents, polymers, fragrances, organic or mineral fillers, thickeners, moisture absorbers or any other ingredient normally used in cosmetics for this type of application.

Needless to say, those skilled in the art will take care to select this or these optional additional compounds such that the advantageous properties intrinsically associated with the cosmetic composition in accordance with the invention are not, or are not substantially, adversely affected by the envisaged addition(s).

According to one particularly preferred form, the composition of the invention also contains at least one thickener.

The thickener may be chosen from polymeric thickeners which are natural or synthetic, anionic, amphoteric, zwitterionic, non-ionic or cationic and associative or non-associative, and non-polymeric thickeners, for instance an electrolyte.

For the purposes of the present invention, the term "associative polymers" is intended to mean hydrophilic polymers that are capable, in an aqueous medium, of reversibly combining with each other or with other molecules. Their chemical structure more particularly comprises at least one hydrophilic region and at least one hydrophobic region.

The term "hydrophobic group" is intended to mean a radical or polymer comprising a saturated or unsaturated and linear or branched hydrocarbon-based chain. When the hydrophobic group denotes a hydrocarbon-based radical, it comprises at least 10 carbon atoms, preferably from 10 to 30 carbon atoms, in particular from 12 to 30 carbon atoms and more preferably from 18 to 30 carbon atoms. Preferentially, the hydrocarbon-based group is derived from a monofunctional compound.

As polymeric thickeners, mention may be made, for example, of cellulose-based thickeners, for example hydroxyethylcellulose, hydroxypropylcellulose and carboxymethylcellulose; guar gum and derivatives thereof, for example hydroxypropyl guar, sold by the company Rhodia under the reference Jaguar HP 105®; gums of microbial origin, such as xanthan gum and scleroglucan gum; carrageenans, for example powdered carrageenan, in particular kapa carrageenan and iota carrageenan, for instance Satiagel VP614® sold by the company Cargill; alginates, for instance Satialgine US 171 EP, Algogel VPC and 0731 Algogel 6021® sold by the company Cargill; glucomannans, for instance the konjac gum KG120AAT® sold by Kevin Food Ingredient; porphyridium polysaccharides, for instance Alguard PF® sold by Fritarom; synthetic polymeric thickeners resulting from radical polymerisation reactions or from polycondensation reactions, such as crosslinked homopolymers of acrylic acid or of acrylamidopropanesulfonic acid, for example Carbomer, for example Carbopol 980® sold by Lubrizol, non-ionic crosslinked homopolymers, such as crosslinked polyvinylpyrrolidone, for instance Flexithix from the company Ashland; associative polymers which are non-ionic, including polyurethanes, which are anionic or which are amphoteric, such as the Acrylates/C10-C30 Alkyl Acrylate Crosspolymer polymers sold under the names Pemulen TR1® or Pemulen TR2® by the company Lubrizol; Acrylates/Steareth-20 Methacrylate Copolymer (Aculyn 22 Polymer®), Acrylates/Beheneth-25 Methacrylate Copolymer (Aculyn 28 Polymer®), Acrylates Copolymer (Aculyn 33 Polymer), PEG-150/Decyl Alcohol/SMDI Copolymer (Aculyn 44 Polymer®) or PEG-150/Stearyl Alcohol/SMDI Copolymer (Aculyn 46 Polymer®) by the company Dow Chemical, the polycondensate of polyethylene glycol comprising 136 mol of ethylene oxide, of stearyl alcohol polyoxyethylenated with 100 mol of ethylene oxide, and of hexamethylene diisocyanate (HDI) having a weight-average molecular weight of 30 000 (INCI name: PEG-136/Steareth-100I/SMDI Copolymer) sold under the trade name Rheolat FX 1100® from the company Elementis and the copolymer of ammonium acryloyldimethyltaurate, of dimethylacrylamide, of lauryl methacrylate and of laureth-4 methacrylate crosslinked with trimethylolpropane triacrylate having the INCI name: Crosspolymer-6 sold under the trade name SEPIMAX ZEN® by the company SEPPIC; acrylic acid homopolymers, in particular chosen from sodium polyacrylates and potassium polyacrylates, preferably sodium polyacrylate, such as the product sold by the company Sensient under the trade reference Covacryl MV 60® or else under the trade name Cosmedia® by Cognis; cationic polymers, for instance quaternary polymers of vinylpyrrolidone, of 1-methyl-3-vinylimidazoline chloride, of vinylimidazole and of methacrylic acid (INCI name Polyquaternium 86), such as the commercial product sold under the name Luvigel Advanced® by the company BASF.

According to one particular form of the invention, an at least partially neutralised acrylic acid homopolymer, in particular chosen from sodium polyacrylates and potassium polyacrylates, preferably sodium polyacrylate, such as the product sold by the company Sensient under the trade reference Covacryl MV 60® or else under the trade name Cosmedia® by Cognis, is used as thickener.

According to one particular form of the invention, a starch modified by crosslinking with functional agents capable of reacting with the hydroxyl groups of the starch molecules, which will thus bond together (for example with glyceryl and/or phosphate groups), is used as thickener.

Monostarch phosphates (of the type $A_m$-O—PO—$(OX)_2$), distarch phosphates (of the type $A_m$-O—PO—(OX)—O-$A_m$) or even tristarch phosphates (of the type $A_m$-O—PO—(O—Am)$_2$) or mixtures thereof ($A_m$ meaning starch) may in particular be obtained by crosslinking with phosphorus compounds.

X in particular denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Use will preferentially be made of distarch phosphates or compounds rich in distarch phosphate, in particular the hydroxypropyl ethers of distarch phosphate having the INCI name: Hydroxypropyl Starch Phosphate, for instance the products sold under the trade names Farinex VA70 C or Farmal MS 689 ® from the company AVEBE Stadex; or the products sold under the trade names Structure BTC®, Structure HVS®, Structure XL® or STRUCTURE ZEA® from National Starch (maize distarch phosphate).

When it contains some, the composition comprises one or more thickeners, preferably polymeric thickeners, in a content ranging from 0.1% to 10% by weight, preferably in a content ranging from 0.2% to 5% by weight, relative to the total weight of the composition.

Fillers

According to one particular form of the invention, the composition according to the invention comprises at least one filler other than the hydrophobic silica aerogel particles of the invention.

The term "filler" should be understood as meaning colourless or white, mineral or synthetic particles of any shape, which are insoluble in the medium of the composition, irrespective of the temperature at which the composition is manufactured.

The composition according to the invention comprises a particulate phase comprising at least one filler other than the hydrophobic aerogel particles of the invention.

The fillers may in particular be organic particles and/or inorganic particles.

Organic Powders

The compositions according to the invention may also contain at least one organic powder. In the present application, the term "organic powder" is intended to mean any organic solid which is insoluble in the medium at ambient temperature (25° C.).

The term "organic powder" is intended to mean any compound or polymer of which the chemical structure comprises at least one or more carbon atoms.

As organic powders that may be used in the composition of the invention, examples that may be mentioned include polyamide particles and in particular those sold under the name Orgasol® by the company Atochem; polyethylene powders; microspheres based on acrylic copolymers, such as those made of ethylene glycol dimethacrylate/lauryl methacrylate copolymer sold by the company Dow Corning under the name Polytrap®; polymethyl methacrylate microspheres, sold under the name Microsphere M-100® by the company Matsumoto or under the name Covabead LH85® by the company Wackherr; ethylene-acrylate copolymer powders, such as those sold under the name Flobeads® by the company Sumitomo Seika Chemicals; expanded powders such as hollow microspheres and in particular microspheres formed from a terpolymer of vinylidene chloride, acrylonitrile and methacrylate and sold under the name Expancel® by the company Kemanord Plast under the references 551 DE 12® (particle size of about 12 µm and mass per unit volume of 40 kg/m3), 551 DE 20® (particle size of about 30 µm and mass per unit volume of 65 kg/m3), 551 DE 50® (particle size of about 40 µm), or the microspheres sold under the name Micropearl F 80 ED® by the company Matsumoto; powders of natural organic materials such as starch powders, in particular of crosslinked or non-crosslinked corn, wheat or rice starch, the powders of starch crosslinked with octenylsuccinic anhydride, sold under the name Dry-Flo® by the company National Starch; silicone resin microbeads such as those sold under the name Tospearl by the company Toshiba Silicone, in particular Tospearl 240; amino acid powders such as the lauroyllysine powder sold under the name Amihope LL-11® by the company Ajinomoto; particles of wax microdispersion, which preferably have mean sizes of less than 1 µm and in particular ranging from 0.02 µm to 1 µm, and which are formed essentially from a wax or a mixture of waxes, such as the products sold under the name Aquacer by the company Byk Cera, and in particular: Aquacer 520 (mixture of synthetic and natural waxes), Aquacer 514® or 513® (polyethylene wax), Aquacer 511® (polymeric wax), or such as the products sold under the name Jonwax 120 by the company Johnson Polymer (mixture of polyethylene wax and paraffin wax) and under the name Ceraflour 961® by the company Byk Cera (micronized modified polyethylene wax); and mixtures thereof.

Inorganic Powders

The term "inorganic powder" is intended to mean any compound or polymer of which the chemical structure does not comprise a carbon atom.

As an example of an inorganic powder, mention may be made of porous spherical silica particles having a mean particle size ranging from 0.5 to 20 µm and more particularly from 3 to 15 µm.

In the present application, the term "spherical particles" is intended to mean particles in the form or substantially in the form of a sphere, which are insoluble in the medium of the composition according to the invention, even at the melting point of the medium (about 100° C.).

They preferably have a specific surface area ranging from 50 to 1000 $m^2/g$ and more particularly from 150 to 800 $m^2/g$. They preferably have a specific pore volume ranging from 0.5 to 5 ml/g and more particularly from 1 to 2 ml/g.

By way of example of porous silica microbeads, use may be made of the following commercial products:
Silica Beads SB 150 from Myoshi
Sunsphere H-51 from Asahi Glass
Sunsil 130 from Sunjin
Spherica P-1500 from Ikeda Corporation
Sylosphere from Fuji Silysia.

Mention may also be made of lamellar inorganic particles, such as talcs, micas or nacres, and mixtures thereof.

Talcs are hydrated magnesium silicates usually comprising aluminium silicate. The crystal structure of talc consists of repeated layers of a sandwich of brucite between layers of silica.

More particularly, the lamellar particles will be chosen from talcs.

Advantageously, use is more particularly made, in the composition of the invention, as lamellar particles, of talc, such as the products sold under the names Rose Talc and Talc SG-2000 by the company Nippon Talc; mica, such as the products sold under the names Mica M RP and Silk Mica by the company Merck; titanium oxide-coated micas, such as mica/titanium oxide/brown iron oxide (CTFA: Mica/Iron oxides/Titanium dioxide), sold under the name Cloisonne Rouge Flambe 440 X by the company Engelhard.

Among the inorganic powders, mention may be made of perlite particles and preferably expanded perlite particles.

The perlites which can be used according to the invention are generally aluminosilicates of volcanic origin and have the composition:

70.0-75.0% by weight of silica $SiO_2$
12.0-15.0% by weight of oxide of aluminium oxide $Al_2O_3$
3.0-5.0% of sodium oxide $Na_2O$
3.0-5.0% of potassium oxide $K_2O$
0.5-2% of iron oxide $Fe_2O_3$→
0.2-0.7% of magnesium oxide MgO
0.5-1.5% of calcium oxide CaO
0.05-0.15% of titanium oxide $TiO_2$ The perlite is ground, dried and then calibrated in a first stage. The product obtained, known as perlite ore, is grey-coloured and has a size of the order of 100 µm.

The perlite ore is subsequently expanded (1000° C./2 seconds) to give more or less white particles. When the temperature reaches 850-900° C., the water trapped in the structure of the material evaporates and brings about the expansion of the material, with respect to its original volume. The expanded perlite particles in accordance with the invention may be obtained via the expansion process described in U.S. Pat. No. 5,002,698.

Preferably, the perlite particles used will be ground; in this case, they are known as Expanded Milled Perlite (EMP). They preferably have a particle size defined by a median diameter $D_{50}$ ranging from 0.5 to 50 µm and preferably from 0.5 to 40 µm.

Preferably, the perlite particles used have an untamped apparent density at 25° C. ranging from 10 to 400 kg/m³ (standard DIN 53468) and preferably from 10 to 300 kg/m³.

Preferably, the expanded perlite particles according to the invention have a water absorption capacity, measured at the wet point, ranging from 200% to 1500% and preferably from 250% to 800%.

The wet point corresponds to the amount of water which has to be added to 1 g of particle in order to obtain a homogeneous paste. This method derives directly from the oil uptake method applied to solvents. The measurements are taken in the same manner by means of the wet point and the flow point, which have, respectively, the following definitions:

wet point: weight expressed in grams per 100 g of product corresponding to the production of a homogeneous paste during the addition of a solvent to a powder;

flow point: weight expressed in grams per 100 g of product above which the amount of solvent is greater than the capacity of the powder to retain it. This is reflected by the production of a more or less homogeneous mixture which flows over the glass plate.

The wet point and the flow point are measured according to the following protocol:

Protocol for Measuring the Water Absorption
1) Equipment Used
Glass plate (25×25 mm)
Spatula (wooden shaft and metal part, 15×2.7 mm)
Silk-bristled brush
Balance 2) Procedure The glass plate is placed on the balance and 1 g of perlite particles is weighed out. The beaker containing the solvent and the liquid sampling pipette is placed on the balance. The solvent is gradually added to the powder, the whole being regularly blended (every 3 to 4 drops) with the spatula.

The weight of solvent needed to obtain the wet point is noted. Further solvent is added and the weight which makes it possible to reach the flow point is noted. The average of three tests will be determined.

The expanded perlite particles sold under the trade names Optimat 1430 OR® and Optimat 2550 ® by the company World Minerals, or those sold under the trade name GK-110 Extra Thin® by Langfang Xindazhong Filter, will in particular be used.

Pigments

Besides fillers, the particulate phase of the composition according to the invention may comprise pigments.

The term "pigments" should be understood as meaning mineral or organic particles that are insoluble in the liquid organic phase, and which are intended to colour and/or opacify the composition.

The pigments may be mineral or organic pigments. Pigments that may be used include metal oxides, for instance iron oxides (in particular yellow, red, brown or black iron oxides), titanium dioxides, cerium oxide, zirconium oxide, chromium oxide; manganese violet, ultramarine blue, Prussian blue and ferric blue, and mixtures thereof.

Iron oxide or titanium dioxide pigments are preferably used.

The inorganic fillers and/or the organic fillers in accordance with the present invention are used in the compositions at concentrations preferably ranging from 0.1% to 10% by weight relative to the total weight of the composition, and more particularly from 0.2% to 5% by weight.

Dyes

Besides fillers and pigments, the particulate phase of the invention may comprise dyes.

The composition according to the invention may also comprise water-soluble or liposoluble dyes.

The term "liposoluble dyes" should be understood as meaning compounds that are generally organic, which are soluble in fatty substances such as oils.

The liposoluble dyes are, for example, Sudan red, D&C Red No. 17, D&C Green No. 6, β-carotene, soybean oil, Sudan Brown, D&C Yellow No. 11, D&C Violet No. 2, D&C Orange No. 5, quinoline yellow, annatto and bromo acids.

Galenical Forms

The composition according to the invention may be in the form of a more or less thick liquid, such as a serum, a gel, a cream or a paste. It may be dispensed in a tube, a device fitted with a grille; in the form of a roll-on (packaged in ball form); in non-aerosol pressurised form, for instance a spray, and may contain in this regard the ingredients generally used in products of this type which are well-known to those skilled in the art.

EXAMPLE 1 (OUTSIDE THE INVENTION): ANHYDROUS SOFT SOLID ACCORDING TO APPLICATION WO2012/084522

| Phase | INCI name (EU) | Concentration |
|---|---|---|
| A | ALUMINIUM ZIRCONIUM TETRACHLOROHYDREX GLY | 20 |
|   | CALCIUM HYDROXIDE | 0.5 |
| B | SILICA SILYLATE (VM-2270 ® - Dow Corning) | 2 |
| C | DIMETHICONE (and) DIMETHICONE CROSSPOLYMER (DC 9041 ® Dow Corning) | 2 |
|   | HYDROGENATED POLYDECENE | 26.3 |
|   | PPG-14 BUTYL ETHER | 2 |
|   | DIMETHICONE | 39.7 |
| D | TRIBEHENIN | 6 |
|   | $C_{18}$-$C_{36}$ ACID TRIGLYCERIDE | 1.5 |
|   | Total | 100 |

Under a hood, the aerogel VM-2270® is made into a paste (phase B) in a part of the oily phase (phase C). The AZG complex is mixed with the calcium hydroxide (phase A), using an ultraturrax, in the rest of the oil mixture (phase C).

Under hot conditions, in a Rayneri mixer: the waxes are melted (phase D), then the aerogel paste followed by the AZG/calcium hydroxide dispersed in the oils are added. The mixture is heated to 75° C. and cast in packs. Cooling to ambient temperature is carried out.

EXAMPLE 2 (OUTSIDE THE INVENTION): DEODORANT ANHYDROUS ROLL-ON ACCORDING TO APPLICATION WO 2012/084520

| INCI Name | Trade reference | % by weight |
|---|---|---|
| POLYDIMETHYLSILOXANE (VISCOSITY: 10 cSt) | DOW CORNING SH 200 C FLUID 10 CS ® (Dow Corning) | 35 |
| ISOPROPYL MYRISTATE |   | 21 |
| ISOPROPYL PALMITATE | ISOPROPYL PALMITATE (COGNIS) | 24 |
| POLYDIMETHYLSILOXANE (VISCOSITY: 350 cSt) | SILICONE FLUID 350CS ® (Dow Corning) | 9 |
| DIMETHICONE (and) DIMETHICONOL | DOW CORNING 1501 FLUID ® (Dow Corning) | 5 |
| SILICA AEROGEL | VM-2270 ® (Dow Corning) | 6 |

The hydrophobic silica aerogel is dispersed in the mixture of the other starting materials using an ultraturrax. A soft paste, which flows under its own weight, is obtained and packaged in a roll-on.

EXAMPLE 3: GEL COMPRISING THE AEROGEL (INVENTION)

| Phase | INCI name (EU) | Concentration |
|---|---|---|
| A | SODIUM POLYACRYLATE [1] | 1 |
|   | AQUA | qs for 100 |
|   | GLYCERIN | 2 |
| B | PROPYLENE GLYCOL | 40 |
|   | CAPRYLOYL SALICYLIC ACID [3] | 0.3 |
|   | SILICA SILYLATE [2] | 2 |
|   | DENATURATED ALCOHOL | 4 |

[1] Cosmedia SP ® (SENSIENT)
[2] Aerogel VM2270 ®(DOW CORNING)
[3] MEXORYL SAB ® (MERCK)

Preparation Phase A: The sodium polyacrylate was sprinkled onto a mixture of water and glycerol and stirred until a homogeneous gel was obtained.

Preparation Phase B: The propylene glycol, the silica silylate, the alcohol and the capryloylsalicylic acid were mixed until a homogeneous phase was obtained. Using a Rayneri mixer and under cold conditions, B was added to A and the mixture was stirred until a colourless homogeneous formula was obtained.

Sensory Test

A comparative sensory test between the compositions according to Examples 1, 2 and 3 was carried out on a panel of 8 individuals. The results are given in the table below:

| Formula | Dry feel | Freshness | Greasy feel |
|---|---|---|---|
| Example 1 Anhydrous Soft Solid (outside the invention) | Dry | No freshness | Greasy |
| Example 2 Anhydrous Roll-on (outside the invention) | Not dry | No freshness | Very greasy |
| Example 3 (invention) | Slightly dry | Very fresh | Slightly greasy |

EXAMPLE 4 (INVENTION)

| Phase | Ingredients | Concentration |
|---|---|---|
| A | HYDROXYPROPYL STARCH PHOSPHATE [1] | 4 |
|   | AQUA | qs for 100 |
|   | GLYCERIN | 2 |
|   | ZINC PIDOLATE [3] | 1 |
| B | PROPYLENE GLYCOL | 40 |
|   | SILICA SILYLATE [2] | 2 |
|   | DENATURATED ALCOHOL | 4 |

[1] Zea Structure ® (AKZO)
[2] Aerogel VM2270 ® (DOW CORNING)
[3] Zincidone ®(UCIB)

Preparation of phase A: the hydroxypropyl starch phosphate was sprinkled onto a mixture of water, glycerol and zinc pidolate and the mixture was stirred until a homogeneous gel was obtained.

Preparation of phase B: the propylene glycol, the silica silylate and the alcohol were mixed until a homogeneous phase was obtained.

Using a Rayneri mixer and under cold conditions, B was added to A and the mixture was stirred until a colourless homogeneous formula was obtained.

EXAMPLE 5 (INVENTION)

| Phase | Ingredients | Concentration |
|---|---|---|
| A | HYDROXYPROPYL STARCH PHOSPHATE [1] | 4 |
|   | AQUA | qs for 100 |
|   | GLYCERIN | 2 |
|   | ALUMINIUM CHLOROHYDRATE [2] | 30 |
| B | PROPYLENE GLYCOL | 40 |
|   | SILICA SILYLATE [3] | 2 |
|   | DENATURATED. ALCOHOL | 4 |

[1] Zea Structure ® (AKZO)
[2] CHLORUDOL 50 ® aqueous solution at 50% by weight (SUMMEREHEIS)
[3] Aerogel VM2270 ® (DOW CORNING)

Preparation of phase A: the hydroxypropyl starch phosphate was sprinkled onto a mixture of water, glycerol and aluminium chlorohydrate and the mixture was stirred until a homogeneous gel was obtained.

Preparation of phase B: The propylene glycol, the silica silylate and the alcohol were mixed until a homogeneous phase was obtained.

Using a Rayneri mixer and under cold conditions, B was added to A and the mixture was stirred until a colourless homogeneous formula was obtained.

EXAMPLE 6 (INVENTION)

| Phase | Ingredients | Concentration |
|---|---|---|
| A | HYDROXYPROPYL STARCH PHOSPHATE [1] | 4 |
|   | AQUA | qs for 100 |
|   | GLYCERIN | 2 |
|   | CALCIUM CHLORIDE [2] | 9.5 |
| B | PROPYLENE GLYCOL | 40 |
|   | SILICA SILYLATE [3] | 2 |
|   | DENATURATED ALCOHOL | 4 |

[1] Zea Structure ®(AKZO)
[2] Calcium Chloride 2H$_2$O (MERCK)
[3] Aerogel VM2270 ® (DOW CORNING)

Preparation of phase A: the hydroxypropyl starch phosphate was sprinkled onto a mixture of water, glycerol and calcium chloride and the mixture was stirred until a homogeneous gel was obtained.

Preparation of phase B: the propylene glycol, the silica silylate and the alcohol were mixed until a homogeneous phase was obtained.

Using a Rayneri mixer and under cold conditions, B was added to A and the mixture was stirred until a colourless homogeneous formula was obtained.

The invention claimed is:

1. A composition comprising, in a cosmetically acceptable medium:
   a) an aqueous phase;
   b) hydrophobic silica aerogel particles;
   c) at least one alcohol of formula (I) below or optical isomers thereof:

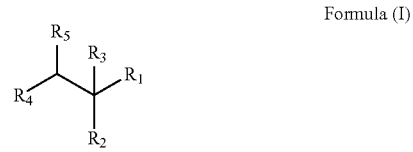

Formula (I)

$R_1$ represents an —OH or CH$_2$OH group;
$R_2$ represents a hydrogen atom or an —OH group;
$R_3$ represents a hydrogen atom or a linear or branched, saturated or unsaturated $C_1$-$C_{22}$ alkyl group;
$R_4$ represents a hydrogen atom, an —OH group, a —CH$_2$OH group, a —CH(OH)—CH$_3$ group, a —C(CH$_3$)$_2$—OH group, a —(O—CH$_2$—CH$_2$)$_n$—OH group, a —(O—CH$_2$—CH(CH$_3$))$_m$—OH group or a —(CH$_2$—CH$_2$)$_p$—OH group;
n denotes an integer ranging from 1 to 10;
m denotes an integer ranging from 1 to 10;
p denotes an integer ranging from 1 to 5;
with the proviso that at least one of the radicals $R_1$, $R_2$, $R_3$ and $R_4$ comprises at least one hydroxyl function;
$R_5$ represents a hydrogen atom or a linear or branched, saturated or unsaturated $C_1$-$C_{22}$ alkyl group and
   d) at least one deodorant active agent other than said alcohol of formula (I) and/or at least one antiperspirant active agent; said hydrophobic silica aerogel particles being dispersed in the aqueous phase.

2. The composition according to claim 1, in which the hydrophobic aerogel particles have a specific surface area per unit of mass (SM) ranging from 500 to 1500 m$^2$/g, and have a size, expressed as the mean diameter (D[0.5]), ranging from 1 to 30 μm and/or an oil absorption capacity, measured at the wet point, ranging from 5 to 18 ml/g of particles.

3. The composition according to claim 1, wherein the hydrophobic silica aerogel particles have a size, expressed as the mean diameter, ranging from 5 to 25 μm.

4. The composition according to claim 1, wherein the hydrophobic silica aerogel particles are particles of hydrophobic silica modified at the surface with trimethylsilyl groups.

5. The composition according to claim 1, wherein the hydrophobic silica aerogel particles have a tamped density p ranging from 0.04 g/cm$^3$ to 0.10 g/cm$^3$.

6. The composition according to claim 1, wherein the hydrophobic silica aerogel particles have a specific surface area per unit of volume SV ranging from 5 to 60 m$^2$/cm$^3$.

7. The composition according to claim 1, wherein the at least one alcohol of formula (I) is chosen from ethanol, propylene glycol, 1,3-butylene glycol, pentylene glycol, hexylene glycol, dipropylene glycol, propane-1,3-diol, polyethylene glycol 8, glycerol and mixtures thereof.

8. The composition according to claim 1, wherein the at least one alcohol of formula (I) is present in a content of from 0.1% to 80% by weight of the composition.

9. The composition according to claim 1, wherein the aqueous phase represents at least 90% by weight relative to the total weight of the composition.

10. The composition according to claim 1, wherein the deodorant agent is chosen from zinc pidolate, calcium chloride, zinc gluconate, triethyl citrate, 5-n-caproyloylsalicylic acid or mixtures thereof.

11. The composition according to claim 1, wherein the antiperspirant agent is chosen from aluminium and/or zirconium salts; complexes of zirconium hydroxychloride and of aluminium hydroxychloride with an amino acid.

12. The composition according to claim 1, also comprising at least one polymeric or non-polymeric thickener.

13. The composition according to claim 12, in which the thickener is an at least partially neutralized acrylic acid homopolymer.

14. The composition according to claim 12, in which the thickener is chosen from distarch phosphates or compounds containing distarch phosphate.

15. The composition according to claim 1 packaged in a tube; in ball form or in non-aerosol pressurized form.

16. A cosmetic treatment process for a keratin material for treating body odours associated with human perspiration, which consists in applying, to the surface of said keratin material to be treated, a composition as defined according to claim 1.

17. The composition according to claim 2, wherein the hydrophobic silica aerogel particles have a size, expressed as the mean diameter, ranging from 5 to 25 μm.

18. The composition according to claim 2, wherein, in which the hydrophobic silica aerogel particles are particles of hydrophobic silica modified at the surface with trimethylsilyl groups.

19. The composition according to claim 3, wherein, in which the hydrophobic silica aerogel particles are particles of hydrophobic silica modified at the surface with trimethylsilyl groups.

20. The composition according to claim 2, wherein the hydrophobic silica aerogel particles have a tamped density p ranging from 0.04 $g/cm^3$ to 0.10 $g/cm^3$.

21. The composition according to claim 1, wherein the aqueous phase represents 90% to 98% by weight relative to the total weight of the composition.

22. The composition according to claim 1, wherein the aqueous phase represents at least 90% by weight relative to the total weight of the composition; the at least one alcohol of formula (I) is present in a content of 0.1% to 80% by weight of the total weight of the composition; the hydrophobic silica aerogel particles are present in a content of 0.05 to 10% by weight relative to the total weight of the composition; the at least one deodorant active agent when present is present in a content of 0.001% to 40% by weight of the total weight of the composition and the at least one antiperspirant active agent when present is present in a content of at least 0.5% to 25% by weight of the total weight of the composition.

23. The composition according to claim 1, wherein the aqueous phase represents at least 90% by weight relative to the total weight of the composition; the at least one alcohol of formula (I) is present in a content of 0.5% to 60% by weight of the total weight of the composition; the hydrophobic silica aerogel particles are present in a content of 0.1 to 5% by weight relative to the total weight of the composition; the at least one deodorant active agent when present is present in a content of 0.1% to 25% by weight of the total weight of the composition and the at least one antiperspirant active agent when present is present in a content of at least 0.5% to 25% by weight of the total weight of the composition.

24. The composition according to claim 1, which is not in the form of an oil/water emulsion.

* * * * *